US008865067B2

(12) United States Patent
Olson et al.

(10) Patent No.: US 8,865,067 B2
(45) Date of Patent: *Oct. 21, 2014

(54) COMBINATION OXYGENATOR AND ARTERIAL FILTER DEVICE FOR TREATING BLOOD IN AN EXTRACORPOREAL BLOOD CIRCUIT

(75) Inventors: Robert Olson, Plymouth, MN (US); John L. Knoll, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

This patent is subject to a terminal disclaimer.

(21) Appl. No.: 13/097,301

(22) Filed: Apr. 29, 2011

(65) Prior Publication Data

US 2012/0277654 A1    Nov. 1, 2012

(51) Int. Cl.
| | | |
|---|---|---|
| *A61M 1/00* | (2006.01) | |
| *A61M 37/00* | (2006.01) | |
| *B01D 63/02* | (2006.01) | |
| *A61M 1/36* | (2006.01) | |
| *A61M 1/16* | (2006.01) | |

(52) U.S. Cl.
CPC .......... *A61M 1/1698* (2013.01); *B01D 2319/06* (2013.01); *B01D 63/025* (2013.01); *A61M 1/3627* (2013.01)
USPC .......................................... 422/45; 604/6.09

(58) Field of Classification Search
CPC ............. A61M 1/1698; A61M 1/3627; B01D 2319/06; B01D 63/025
USPC ............ 604/4.01–6.16; 422/44–48; 428/36.3; 98/6
See application file for complete search history.

(56) References Cited

U.S. PATENT DOCUMENTS

| | | | |
|---|---|---|---|
| 4,239,729 A | 12/1980 | Hasegawa et al. | |
| 4,940,617 A * | 7/1990 | Baurmeister | 428/36.3 |
| 4,975,247 A | 12/1990 | Badolato et al. | |
| 5,141,031 A | 8/1992 | Baurmeister | |
| 5,230,862 A | 7/1993 | Berry et al. | |
| 5,462,619 A | 10/1995 | Haworth et al. | |
| 5,651,765 A | 7/1997 | Haworth et al. | |
| 5,762,868 A | 6/1998 | Leonard | |
| 5,762,869 A | 6/1998 | White et al. | |
| 5,770,149 A | 6/1998 | Raible | |
| 5,782,791 A | 7/1998 | Peterson et al. | |
| RE36,125 E | 3/1999 | Haworth et al. | |
| 6,428,747 B1 | 8/2002 | Dueri et al. | |
| 6,454,999 B1 | 9/2002 | Farhangnia et al. | |
| 6,503,450 B1 | 1/2003 | Afzal et al. | |

(Continued)

OTHER PUBLICATIONS

Medtronic brochure entitled "The Affinity Hollow Fiber Oxygenator" UC9804380EN copyright 1999 (6 pages).

(Continued)

*Primary Examiner* — Philip R Wiest

(57) ABSTRACT

A combination oxygenator and arterial filter device for treating blood in an extracorporeal circuit includes a housing, an oxygenator, and a depth filter. The oxygenator includes a hollow fiber bundle forming an oxygenator exterior face. The depth filter is disposed (e.g., wound) directly over the exterior face, and includes a plurality of filaments arranged to define filter layers of level wound filaments. A first layer directly abuts the oxygenator exterior face. The oxygenator bundle differs from the depth filter in terms of: fiber and filament materials, construction of the fibers and filaments, and/or minimum gap spacings between axially adjacent ones of the fibers and the filaments. An oxygenator with integrated arterial filtering capability is provided that minimally impacts the extracorporeal blood circuit prime volume.

28 Claims, 14 Drawing Sheets

(56) References Cited

U.S. PATENT DOCUMENTS

| | | | |
|---|---|---|---|
| 6,723,283 | B2 | 4/2004 | Ghelli et al. |
| 6,730,267 | B2 | 5/2004 | Stringer et al. |
| 6,852,280 | B2 | 2/2005 | Vijay et al. |
| 6,946,099 | B2 | 9/2005 | Vijay et al. |
| 6,960,322 | B2 | 11/2005 | Stringer et al. |
| 6,998,093 | B1 | 2/2006 | McIntosh et al. |
| 7,022,099 | B2 | 4/2006 | Litzie et al. |
| 7,022,284 | B2 | 4/2006 | Brian et al. |
| 7,431,754 | B2 * | 10/2008 | Ogihara et al. ............ 96/8 |
| 7,476,359 | B2 | 1/2009 | Maianti et al. |
| 7,749,435 | B2 | 7/2010 | Ogihara et al. |
| 7,947,113 | B2 | 5/2011 | Ogihara et al. |
| 2004/0219060 | A1 | 11/2004 | Maianti et al. |
| 2006/0008380 | A1 | 1/2006 | Moozyckine et al. |
| 2006/0089586 | A1 | 4/2006 | Kaus et al. |
| 2007/0009378 | A1 | 1/2007 | Blicke et al. |
| 2007/0166189 | A1 | 7/2007 | Ogihara |
| 2007/0166190 | A1 | 7/2007 | Ogihara et al. |
| 2007/0231203 | A1 | 10/2007 | Mizoguchi et al. |
| 2008/0060990 | A1 | 3/2008 | Bernard et al. |
| 2008/0199357 | A1 | 8/2008 | Gellman et al. |
| 2009/0087342 | A1 | 4/2009 | Maianti et al. |
| 2009/0137939 | A1 | 5/2009 | Maianti et al. |
| 2009/0230058 | A1 | 9/2009 | Boris-Moeller |
| 2010/0224559 | A1 | 9/2010 | Ogihara et al. |
| 2010/0274170 | A1 | 10/2010 | Carpenter et al. |

OTHER PUBLICATIONS

Medtronic brochure entitled "Affinity NT Oxygenation Systems" UC200000683EN copyright 1999 (6 pages).

* cited by examiner

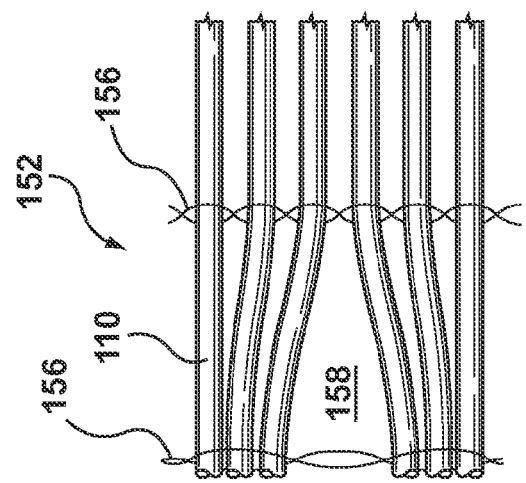
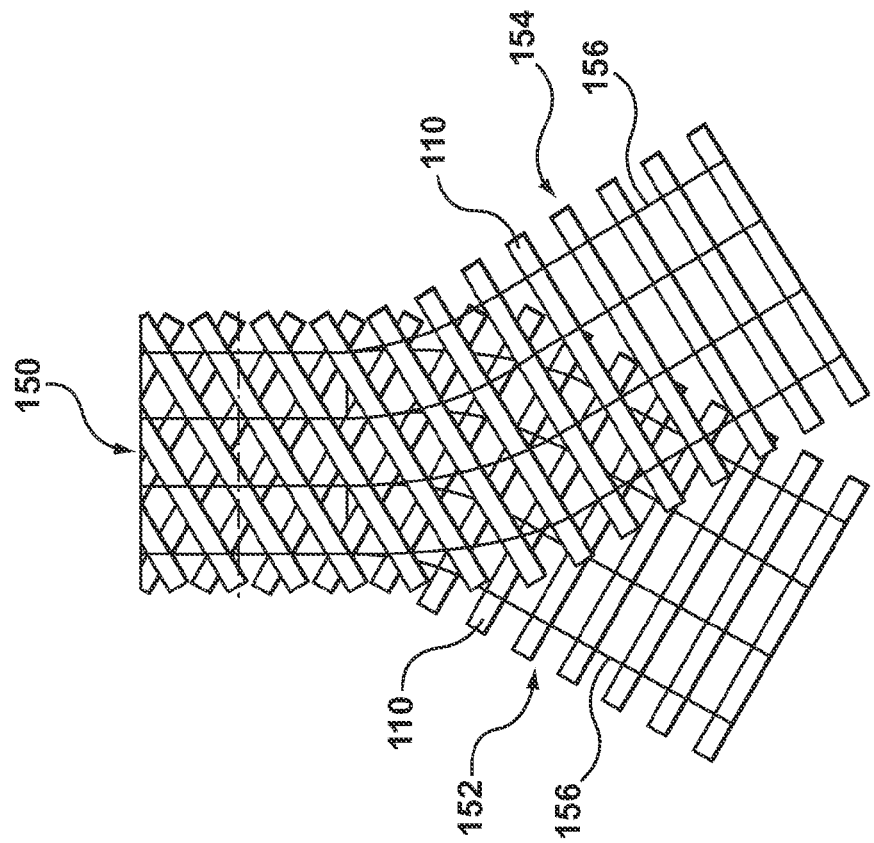

COMBINATION OXYGENATOR AND ARTERIAL FILTER DEVICE FOR TREATING BLOOD IN AN EXTRACORPOREAL BLOOD CIRCUIT

BACKGROUND

The present disclosure relates to extracorporeal blood circuits, systems, and methods of use. More particularly, it relates to devices for oxygenating and filtering blood in an extracorporeal blood circuit, and methods of making such devices.

An extracorporeal blood circuit is commonly used during cardiopulmonary bypass to withdraw blood from the venous portion of the patient's circulation system (via a venous cannula) and return the blood to the arterial portion (via an arterial cannula). The extracorporeal blood circuit generally includes a venous drainage or return line, a venous blood reservoir, a blood pump, an oxygenator, an arterial filter, and blood transporting tubing, ports, and connection pieces interconnecting the components. As shown in FIG. 1, some prior art extracorporeal blood circuits drain venous blood from patient 10 via a venous return line 12. Cardiotomy blood and surgical field debris are aspirated from the patient 10 by a suction device 16 that is pumped by a cardiotomy pump 18 into a cardiotomy reservoir 20. Venous blood from the venous return line 12, as well as de-foamed and filtered cardiotomy blood from the cardiotomy reservoir 20, are discharged into a venous blood reservoir 22. Air entrapped in the venous blood rises to the surface of the blood in the venous blood reservoir 22 and is vented to atmosphere through a purge line 24. A venous blood pump 26 draws blood from the venous blood reservoir 22 and pumps it through an oxygenator 28 and an arterial blood filter 29. An arterial line 14 returns the oxygenated and filtered blood back to the patient's arterial system via an arterial cannula (not shown) coupled to the arterial line 14.

The oxygenator component of the extracorporeal blood circuit is well known. In general terms, the oxygenator takes over, either partially or completely, the normal gas exchange function of the patient's lungs. In oxygenators that employ a microporous membrane, blood is taken from the patient and is circulated through the oxygenator on one side of the membrane. Concurrently, an oxygenating gas is passed through the oxygenator on the other side of the membrane. Carbon dioxide diffuses from the blood across the microporous membrane into the passing stream of oxygenating gas; at the same time, oxygen diffuses from the oxygenating gas across the membrane into the blood. The circulating blood, having thereby been reduced in carbon dioxide content and enriched in oxygen, is returned to the patient. One popular type of membrane oxygenator is referred to as a hollow fiber oxygenator, and is illustrated generally in U.S. Pat. No. 4,239,729. A hollow fiber oxygenator employs a large plurality (typically tens of thousands) of microporous or semipermeable hollow fibers disposed within a housing. These hollow fibers are sealed in end walls of the housing that are then fitted with skirted end caps. One end cap is fitted with an inlet, the other end cap is fitted with an outlet. A peripheral wall of the housing has an inlet located interiorly of one of the end walls and an outlet located interiorly of the other end wall. The oxygenating gas enters the device through the inlet, passes through the lumens of the hollow fibers, and exits the device through the outlet. It will be understood that carbon dioxide diffuses from the blood flowing over the outer surfaces of the hollow fibers through the fiber walls and into the stream of oxygenating gas. At the same time, oxygen from the oxygenating gas flowing through the lumens of the hollow fibers diffuses through the fiber walls and into the blood flowing about the fibers to oxygenate the blood.

A well-accepted technique for forming a hollow fiber oxygenator is to spirally wind ribbons of the fibers about an internal supporting core, as described for example in U.S. Pat. No. 4,975,247. Blood flow through the resultant annular "bundle" of fibers can be in various directions such as radially outward, axial, circumferential, etc. With radially outward flow designs, U.S. Pat. No. 5,462,619 describes an improved winding technique that provides desired pressure drops and minimal clotting risks by a graduated packing fraction. An oxygenator product available from Medtronic, Inc., under the trade name Affinity® NT Oxygenator, is one example of a spirally wound hollow fiber oxygenator with graduated packing fraction.

For purposes of this disclosure, packing fraction is defined to mean the fraction of a unit volume of bundle space occupied by fibers (or filaments). The packing fraction may be determined in ways known in the art, including the convenient method of measuring the interstitial space between fibers (or filaments) by weight gain when a unit volume is primed with a known liquid. Packing fraction at a particular region or zone located radially outward may be determined by stopping the corresponding winding process at the radially inner radial boundary of the region or zone and determining the packing fraction at that stage, and then continuing the winding process to the outer radial boundary of the region or zone and determining the packing fraction at that stage. Computations known in the art will determine the packing fraction of the region or zone using the prior two values.

Arterial filters are also well known, and can take various forms appropriate for air handling and blood filtration. In general terms, the conventional arterial filter device includes one or more screen-type filters within a filter housing that combine to capture and remove particulate (e.g., emboli) on the order of about 20-40 microns and larger, as well as to trap gaseous microemboli larger than a certain size to prevent the emboli from reaching the patient. These emboli can cause significant harm to the patient by plugging small arteries, arterioles, and or capillaries, preventing adequate blood flow to small or large areas of tissue or organs. Examples of known arterial blood filters are described in U.S. Pat. Nos. 5,651,765 and 5,782,791. Arterial blood filters are also available from Medtronic, Inc. under the trade name Affinity® Arterial Filter.

Conventionally, the arterial filter device is fluidly connected within the extracorporeal circuit downstream (or upstream) of the oxygenator device by tubing. While implementation of the separate oxygenator and arterial filter devices as part of an extracorporeal blood circuit is well accepted, certain concerns arise. An arterial filter typically adds 200 ml (or more) of prime volume to the extracorporeal blood circuit; this added prime volume is undesirable as it can lead to increased hemodilution of the patient. As a point of reference, the volume of blood and/or prime solution liquid that is pumped into the extracorporeal blood circuit to "prime" the circuit is referred to as the "prime volume". Typically, the extracorporeal blood circuit is first flushed with $CO_2$ prior to priming. The priming flushes out any extraneous $CO_2$ gas from the extracorporeal blood circuit prior to the introduction of the blood. The larger the prime volume, the greater the amount of prime solution present in the extracorporeal blood circuit that mixes with the patient's blood. The mixing of the blood and prime solution causes hemodilution that is disadvantageous and undesirable because the relative concentration of red blood cells must be maintained during the surgical procedure in order to minimize adverse effects to the patient. It is therefore desirable to minimize the extracorporeal blood circuit's prime volume (and thus the required volume of prime solution).

In light of the above, a need exists for an extracorporeal blood circuit device that provides oxygenation and arterial filtering properties at least commensurate with conventional oxygenator and arterial filter components, yet minimizes the overall impact on the prime volume of the extracorporeal blood circuit.

SUMMARY

Some aspects in accordance with principles of the present disclosure relate to a combination oxygenator and arterial filter device for treating blood in an extracorporeal blood circuit. The device includes a housing, an oxygenator, and a depth filter. The oxygenator is maintained within the housing and includes a plurality of hollow fibers helically wound about an internal core to define an oxygenator bundle forming an oxygenator exterior face. The depth filter is disposed directly over the oxygenator exterior face, and includes a plurality of filaments arranged to define first and second filter layers of level wound filaments (e.g., level cross-wound filaments). The first filter layer directly abuts the oxygenator exterior face, and the second filter layer directly abutting the first layer opposite the oxygenator exterior face. The oxygenator bundle and depth filter can both be annular, defining a common central axis. Regardless, a structure of the oxygenator bundle differs from a structure of the depth filter by at least one characteristic selected from the group consisting of: materials of the fibers and the filaments, construction of the fibers and filaments, and/or minimum gap spacings between adjacent, axially aligned ones of the fibers and minimum gap spacings between adjacent, axially aligned ones of the filaments. In some embodiments, an outer diameter of the depth filter filaments is less than an outer diameter of the oxygenator bundle fibers. In other embodiments, some or all of the depth filter filaments are solid. In yet other embodiments, the oxygenator bundle fibers are formed of a first material and the depth filter filaments are formed of a second material differing from the first material. In yet other embodiments, a minimum gap spacing between axially adjacent filaments of the first filter layer is less than a minimum gap spacing between axially adjacent fibers of the oxygenator bundle. The filaments of the depth filter can be wound over the oxygenator bundle. Alternatively, the filaments can be knitted into a mat or formed into a double weft tape applied over the oxygenator exterior face. With any of these constructions, an oxygenator with integrated arterial filter capability is provided having reduced foreign surface area and reduced impact on the prime volume of the corresponding extracorporeal blood circuit (e.g., on the order of 25 ml or less) as compared to conventional arterial filter devices provided physically apart from the oxygenator.

Yet other aspects in accordance with principles of the present disclosure relate to an extracorporeal blood circuit including a venous line, an arterial line, and a combination oxygenator and arterial filter device. The combination oxygenator and arterial filter device forms an inlet side and an outlet side. The inlet side is fluidly connected to the venous line, that in turn is arranged to receive blood from a patient (e.g., via a pump). Conversely, the outlet side is fluidly connected to the arterial line that in turn is located to deliver blood to the patient. The combined oxygenator and arterial filter device includes the oxygenator bundle and depth filter as described above. In some embodiments, the extracorporeal blood circuit is characterized by the absence of an additional arterial filter between the combination oxygenator and arterial filter device and the arterial line.

Yet other aspects in accordance with principles of the present disclosure relate to a method of making a combination oxygenator and arterial filter device for treating blood in an extracorporeal blood circuit. The method includes helically winding a plurality of hollow semipermable fibers about an internal core to define an oxygenator bundle forming an oxygenator exterior face. A depth filter is applied directly over and in contact with the oxygenator exterior face, with the depth filter including a plurality of filaments arranged to define radially-arranged, first and second filter layers of level wound filaments. The first filter layer abuts the oxygenator exterior face, whereas the second filter layer abuts the first filter layer opposite the oxygenator exterior face. Finally, a structure of the oxygenator bundle differs from a structure of the depth filter by at least one of: the materials of the oxygenator bundle fibers and the depth filter filaments, construction of the oxygenator bundle fibers and the depth filter filaments, and minimum gap spacings between adjacent, axially aligned ones of the depth filter fibers and minimum gap spacings between axially adjacent ones of the depth filter filaments. In some embodiments, the step of applying the depth filter includes helically winding the plurality of filaments over the oxygenator bundle. In related embodiments, the plurality of hollow fibers are helically wound about the internal core by threading a guide tube of a winding apparatus with the hollow fibers and rotating the internal core relative to the guide tube. With these embodiments, subsequent helical winding the plurality of filaments includes removing the hollow fibers from the guide tube, threading at least some of the filaments into the guide tube, and then rotating the internal core relative to the fiber guide tube so as to apply the filaments onto the oxygenator bundle and form the depth filter.

BRIEF DESCRIPTION OF THE DRAWINGS

FIG. 6A is a simplified schematic illustration of another embodiment depth filter useful with the devices of FIGS. 2A-2C;

FIG. 6B is an enlarged view of a portion of the depth filter of FIG. 6A;

DETAILED DESCRIPTION

Figure 1:
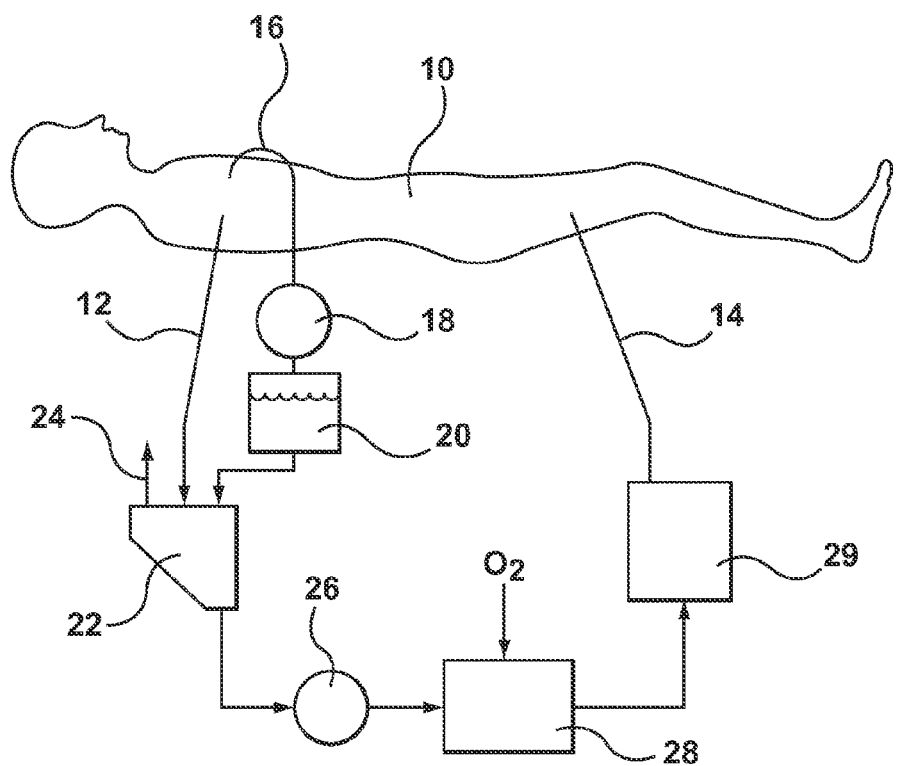
FIG. 1 is a schematic diagram of a prior art extracorporeal blood circuit including separated oxygenator and arterial filter devices.
Figure 2A:
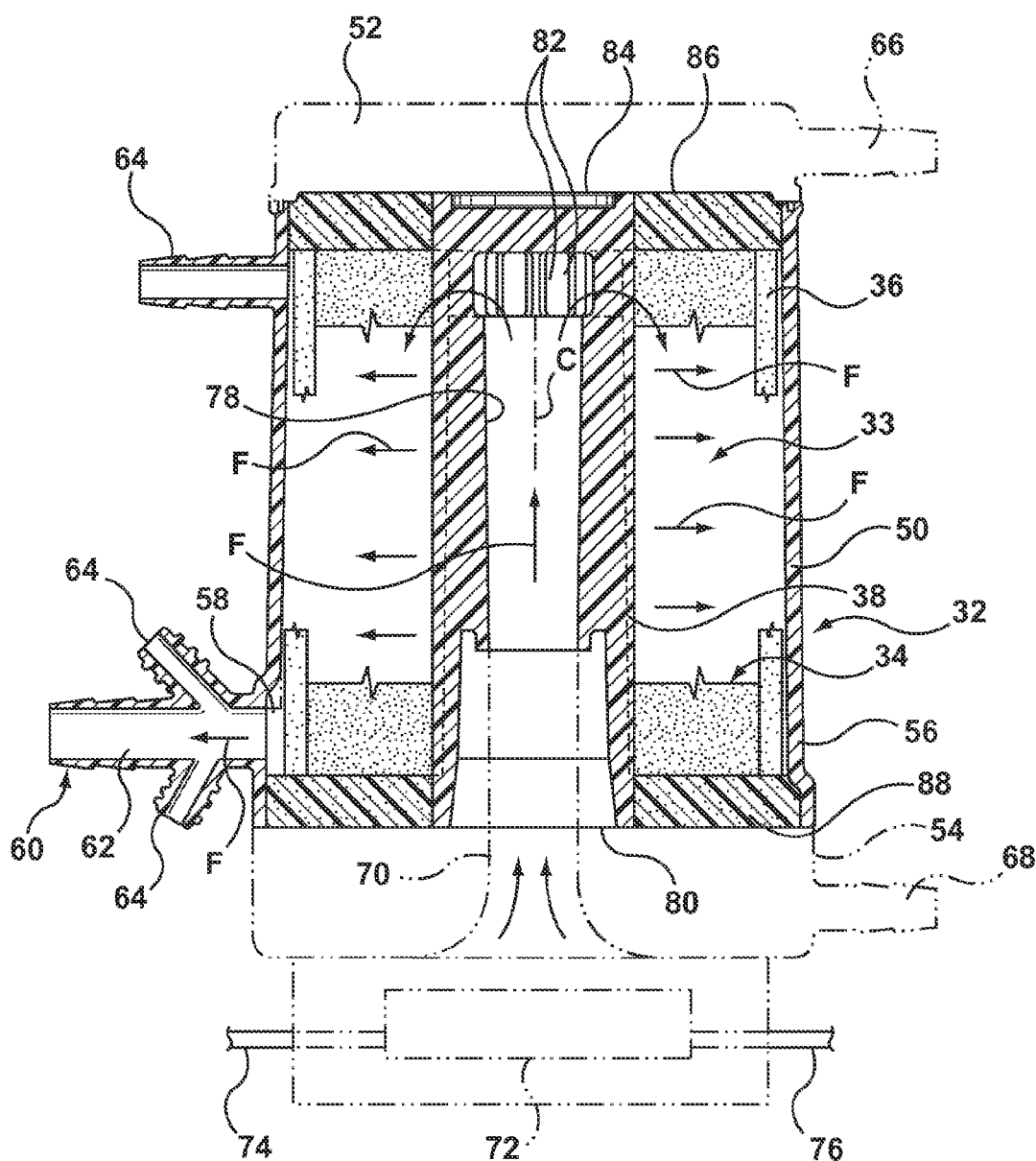
FIG. 2A is a cross-sectional view of a combination oxygenator and arterial filter device in accordance with principles of the present disclosure, depicting the device vertically oriented as it would be in use.

One embodiment of a combination blood oxygenator and arterial filter device 30 in accordance with principles of the present disclosure is shown in FIG. 2A. The device 30 includes a housing 32, an oxygenator 34 (referenced generally) and an arterial depth filter 36 (referenced generally). Details on the various components are provided below. In general terms, however, the oxygenator 34 includes an internal core 38 about which an oxygenator bundle 40 is formed. The depth filter 36 is disposed directly over the oxygenator bundle 40, with the so-constructed oxygenator 34 and depth filter 36 contained within the housing 32. A blood flow path is defined by the housing 32, directing blood flow radially through the oxygenator bundle 40 and then the depth filter 36, with the oxygenator bundle 40 facilitating oxygenation of the supplied venous blood, and the depth filter 36 removing gaseous and particulate microemboli. The device 30 is thus amenable for insertion within an extracorporeal blood circuit as described below, providing necessary oxygenation and filtration capabilities with minimal overall impact on the extracorporeal circuit's prime volume.

The housing 32 can assume various forms, and generally includes or defines an outer wall 50, a gas header or cap 52, and a bottom header or cap 54. The outer wall 50 is sized to contain the oxygenator 34 and the depth filter 36, and can be generally cylindrical. At a base region 56, an optional annular eccentric relieved area 58 forms, or is fluidly connected to, an outlet manifold 60 having a blood outlet 62. Other optional outlets or ports, such as sample or recirculation ports 64, can be provided by the manifold 60 or may be suitably located elsewhere along the outer wall 50.

The gas header 52 is configured for assembly to the outer wall 50, and includes or defines a gas inlet 66. Similarly, the bottom header 54 is configured for assembly to the outer wall 50 opposite the gas header 52, and can form or include a gas outlet 68. The bottom header 54 also includes or defines a blood entrance or inlet 70 for directing a blood flow into the device 30.

Figure 2B:
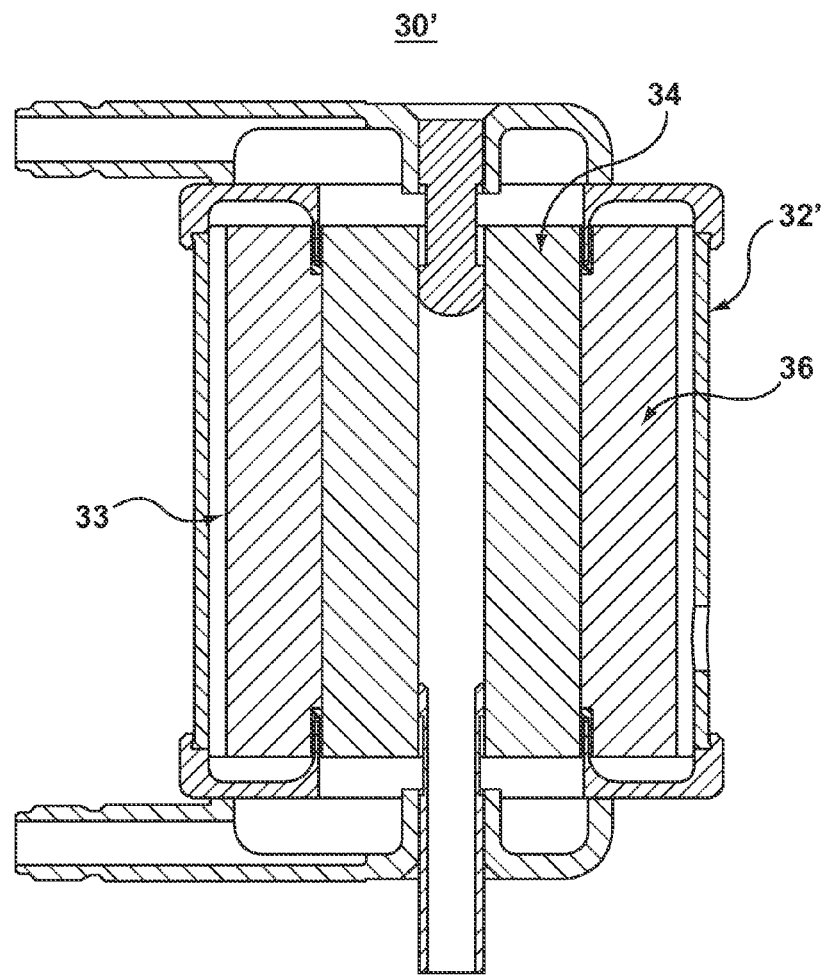
FIG. 2B is a cross-sectional view of another combination oxygenator and arterial filter device in accordance with principles of the present disclosure.
Figure 2C:
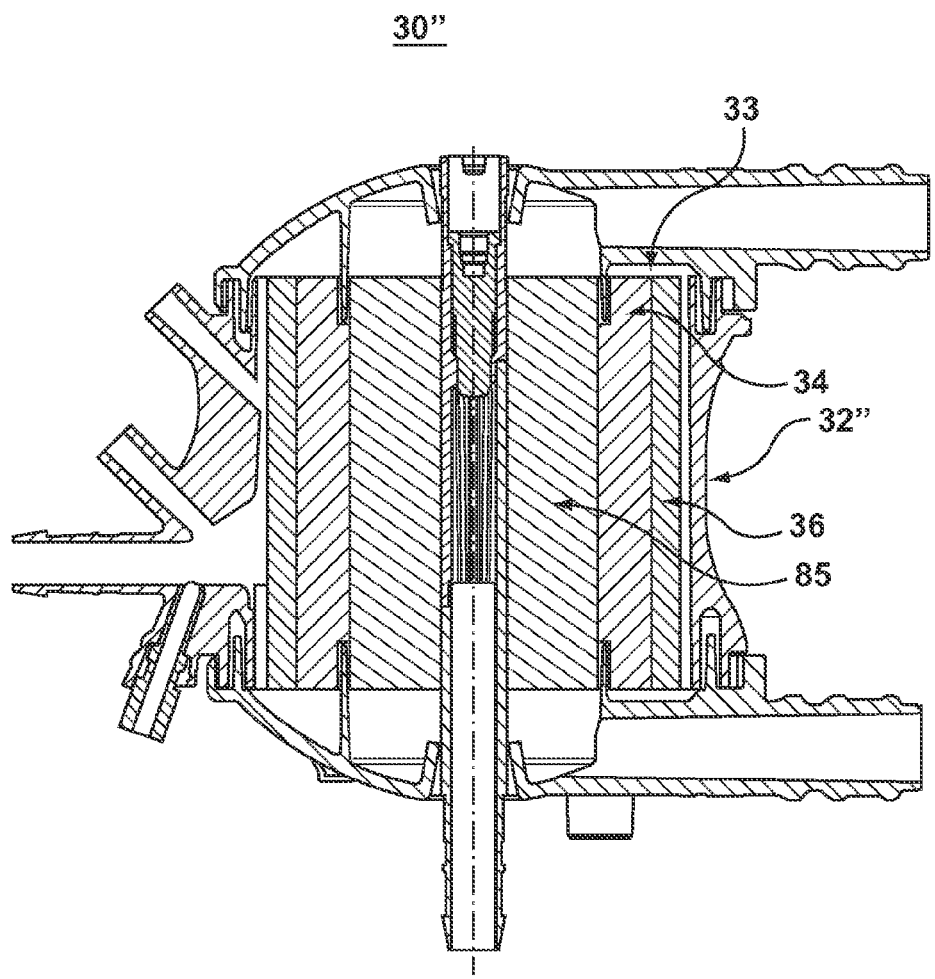
FIG. 2C is a cross-sectional view of another combination oxygenator and arterial filter device in accordance with principles of the present disclosure.

The device 30, at the bottom header 54, can optionally be provided with, or carry, a suitable heat exchanger 72. A fluid type heat exchanger 72 is depicted with a heat exchange fluid inlet 74 and a heat exchange fluid outlet 76, but other suitable heat exchange devices can be incorporated with the device 30, for example an electrical heating and cooling device might be used. In other embodiments, the heat exchanger 72 is omitted. For example, FIG. 2B illustrates an alternative device 30' in accordance with principles of the present disclosure and including the oxygenator bundle 40 and the arterial depth filter 36 within a housing 32'. The device 30' does not include a heat exchanger. Conversely, FIG. 2C illustrates another device 30" in accordance with the principles of the present disclosure and including the oxygenator bundle 40 and the arterial depth filter 36 within a housing 32". Further, a bundled heat exchanger 85 is disposed between the oxygenator bundle 40 and the core 38.

Returning to FIG. 2A and as mentioned above, the oxygenator 34 includes the internal core 38 and the oxygenator bundle 40. The internal core 38 is a generally cylindrical, hollow body, and is configured for winding of (and supporting) the oxygenator bundle 40 about an outer surface thereof. The internal core 38 can optionally incorporate various features (e.g., ribs, flanges, recessed regions, etc.) that promote robust assembly with the oxygenator bundle 40. Regardless, the internal core 38 forms a central passage 78 that is fluidly open to the blood inlet 70 at a first end 80. A chamber 82 is formed adjacent a second end 84 of the core 38, and is fluidly open to an exterior of the internal core 38 by one or more windows (not shown) that dictate a radially outward blood flow path from the passage 78 as reflected by arrows in FIG. 2A.

The oxygenator bundle 40 is an annular bundle of helically-wound, microporous hollow fibers (drawn generally in FIG. 2A, but identified in greater detail below with reference to FIGS. 3A-3C) positioned along the internal core 38. The top and bottom ends of the oxygenator bundle 40 are embedded in solidified potting compositions 86, 88 at top and bottom ends, respectively, of the housing 32. The fiber lumens communicate with the outer surface of the upper and lower potted compositions 86, 88, respectively. An oxygenating gas introduced via the gas inlet 66 flows into the gas header 52, through the lumens of the hollow fibers, down to the opposite ends of the hollow fibers at the lower potted region 88, and into the gas outlet passage 68.

It should be understood that the potting process referred to herein above is a well known fiber potting process in which a potting material (e.g., polyurethane) is introduced by centrifuging and reacted in situ. Other appropriate potting materials may be used. Suitable sealants and gaskets may be used at joints in the housing 32, such as the joints between the top and bottom headers 52, 54 and the outer wall 50. Any suitable microporous fiber may be used in the oxygenator bundle 40; for example, a suitable fiber is the microporous polypropylene fiber available under the trade name CELGARD™ X30 (outer diameter on the order of 200-300 microns) from Membrana of Charlotte, N.C.

The hollow fiber oxygenator bundle 40 extends radially outward relative to a central axis C of the internal core 38. The fibers can include a first plurality of fibers positioned (e.g., wound) helically around the internal core 38 in a first direction from the first end 80 to the second end 84 of the internal core 38, and a second plurality of fibers positioned helically around the internal core 38 in a second direction opposite the first direction, and thus from the second end 84 to the first end 80. Various acceptable methods of winding the microporous fibers about the internal core 38 to generate the oxygenator bundle 40 are described in U.S. Pat. Nos. 4,975,247 and 5,462,619, the entire teachings of both of which are incorporated herein by reference. For example, as described in the '619 Patent, the oxygenator bundle 40 can be wound to define a graduated packing fraction that increases from an inside radius of the oxygenator bundle 40 to the outside radius.

Figure 3A:
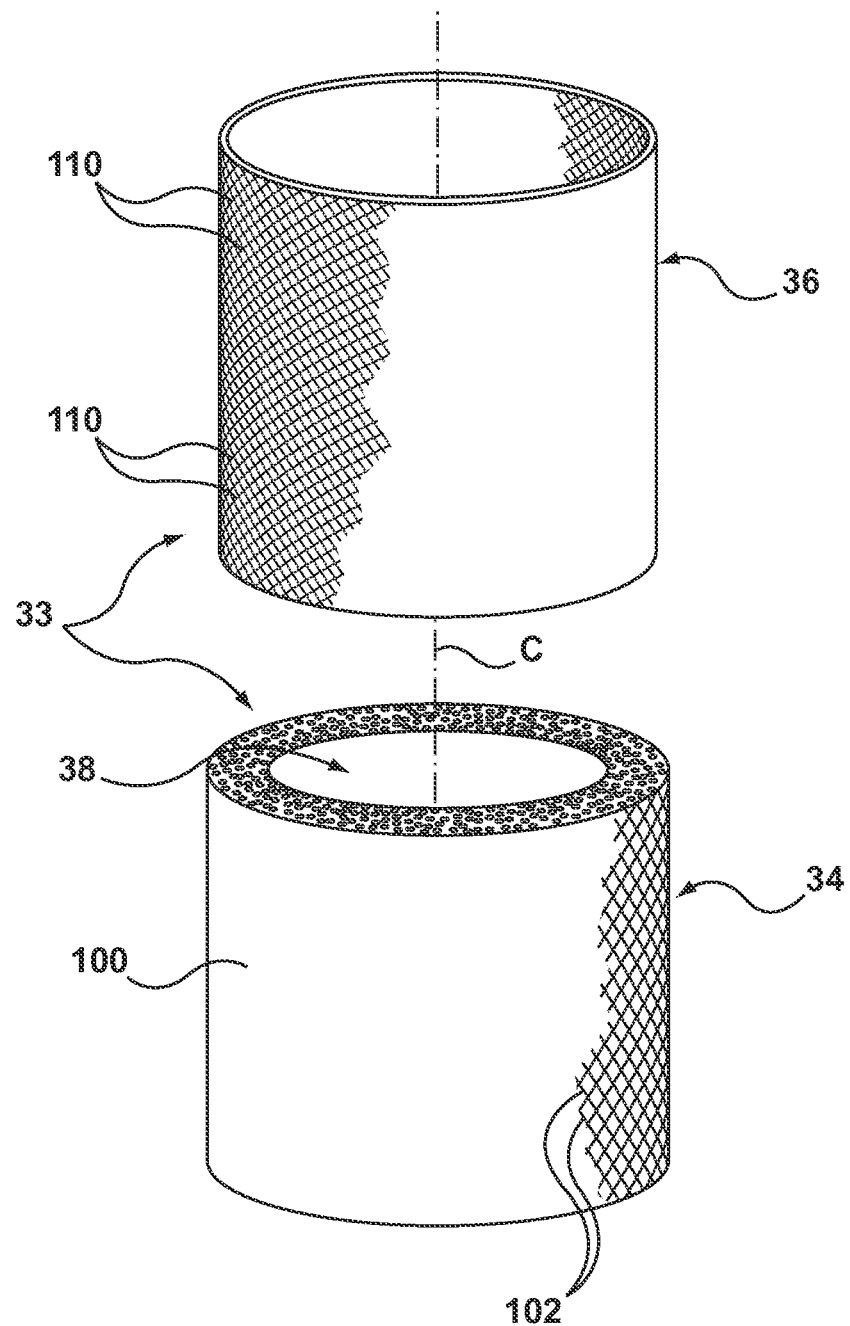
FIG. 3A is a perspective, exploded view of oxygenator bundle and depth filter components of the devices of FIGS. 2A-2C.
Figure 3B:
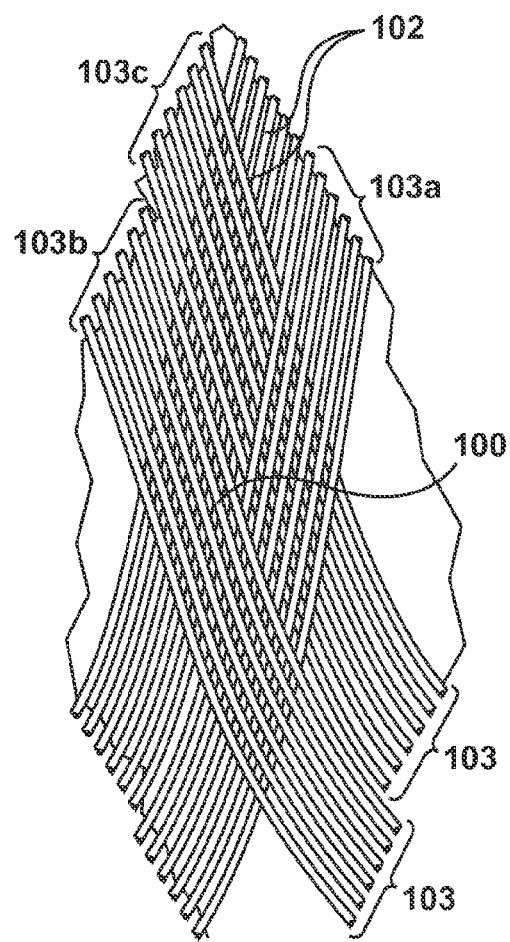
FIG. 3B is a simplified, greatly magnified top plan view of a portion of the oxygenator bundle of FIG. 3A.
Figure 3C:
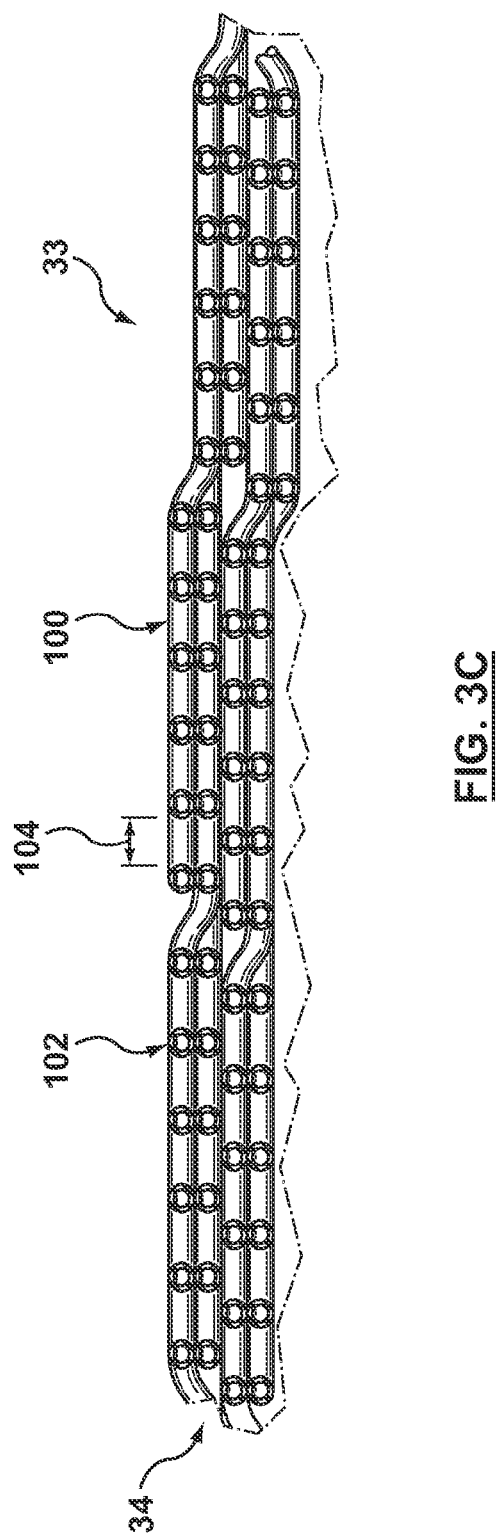
FIG. 3C is a cross-sectional, greatly magnified view of a portion of the oxygenator bundle of FIG. 3A.

Regardless of the packing fraction properties of the oxygenator bundle 40, an oxygenator exterior face 100 is provided, as shown in FIG. 3A. The oxygenator exterior face 100 is defined as the terminal face of the oxygenator bundle 40 opposite the internal core 38 (omitted from the view of FIG. 3A for ease of explanation, but a location of which relative to the oxygenator bundle 40 being generally indicated). The oxygenator exterior face 100 is generally annular, and is comprised of a series of axially or longitudinally adjacent windings of the hollow fibers 102 (a thickness or diameter of which is exaggerated in FIG. 3A for ease of explanation). Commensurate with the above descriptions, individual ones of the hollow fibers 102 may be arranged in differing wind directions along the oxygenator exterior face 100. Further, in some embodiments, selected groupings of the hollow fibers 102 may be collectively cross-wound in identical directions as a fiber ribbon (e.g., as described in the '619 Patent, six continuous hollow fibers are collectively cross-wound as a discernable ribbon). As such, not all of the fibers 102 along the oxygenator exterior face 100 may be precisely axially aligned. For example, FIG. 3B depicts a ribbon 103 of the fibers 102 being collectively cross-wound, with exposed segments 103a, 103b, 103c of the wound fiber ribbon 103 each forming a portion of the oxygenator exterior face 100. However, and as reflected in FIG. 3C, a minimum gap spacing 104 is established between axially adjacent ones of the fibers 102, with the minimum gap spacing 104 being in the range of 20-70 microns in some embodiments, in the range of 30-60 microns in other embodiments, and on the order of 38 microns in other embodiments.

Returning to FIG. 3A, the depth filter 36 is constructed to be directly applied or formed over the oxygenator bundle 40 as described below, and is generally characterized as a radially outward extension from the oxygenator exterior face 100. In particular, the depth filter 36 includes a plurality of filaments 110 (referenced generally) arranged over the oxygenator exterior face 100. The filaments 110 can be made from a plastic resin such as polyester, polypropylene, polyethylene, etc., and can be solid filaments and/or microporous hollow filaments. The filaments 110 may or may not be identical in terms of material, structure, or size, but in some embodiments a maximum outer diameter of the filaments 110 is not greater than about 200 microns; in other embodiments not greater than 150 microns. In yet other embodiments, an outer diameter of the filaments 110 is in the range of 40-50 microns.

Figure 4A:
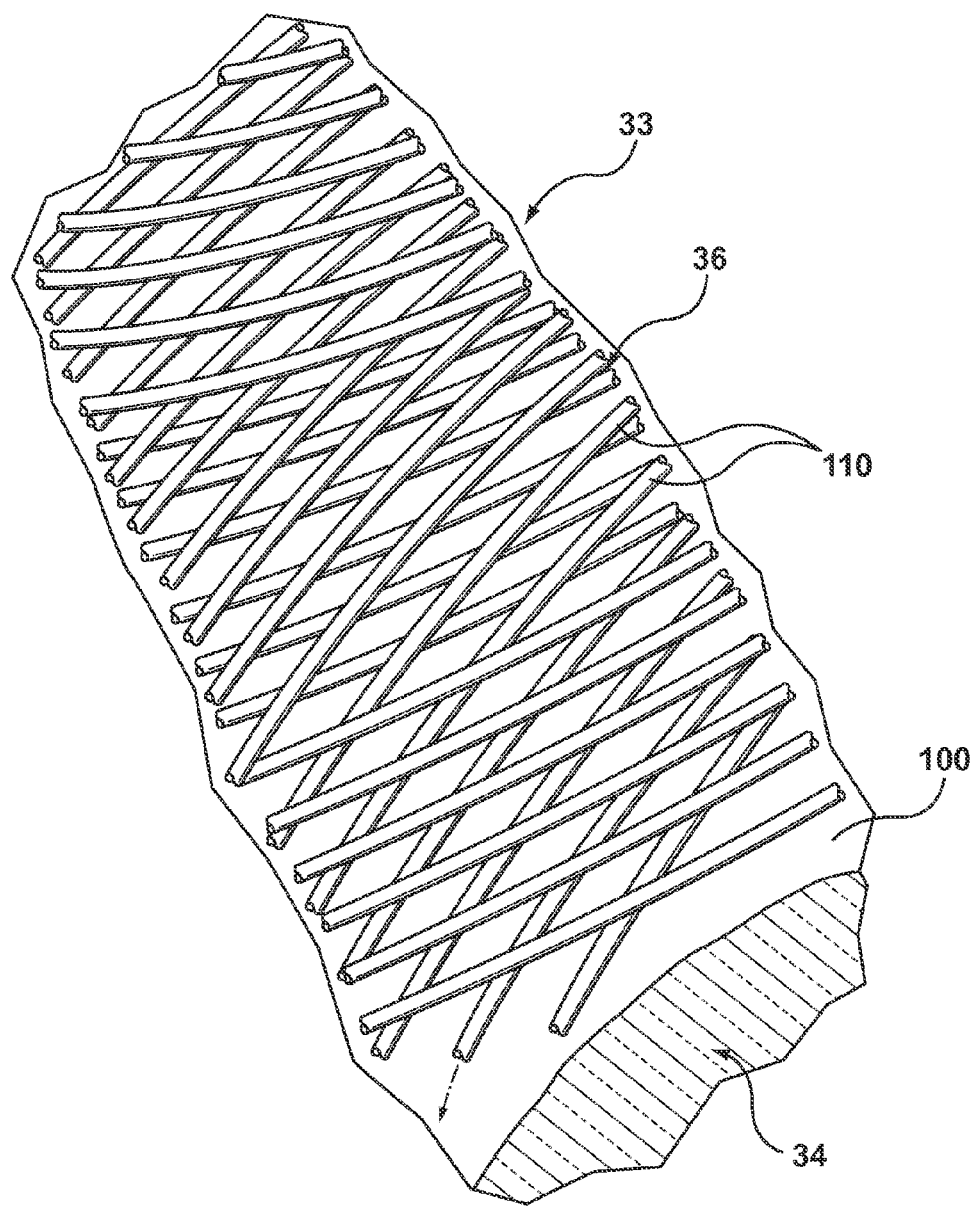
FIG. 4A is a perspective, greatly magnified view of a portion of the devices of FIGS. 2A-2C, illustrating the depth filter of FIG. 3A applied to the oxygenator bundle.
Figure 4B:
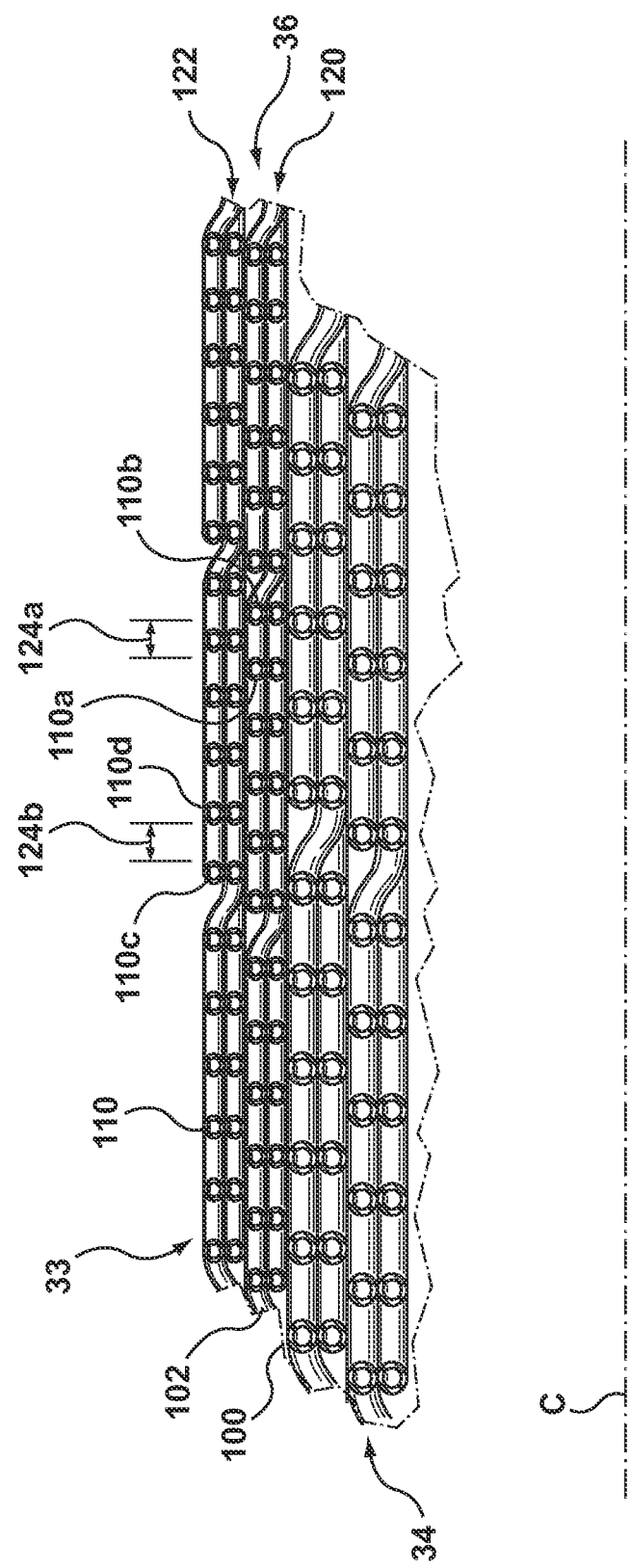
FIG. 4B is a cross-sectional, greatly magnified view of a portion of the depth filter of FIG. 4A.

Regardless of an exact construction and/or materials of the filaments 110, the filaments 110 are arranged over the oxygenator exterior face 100 so as to define level cross-wound filter layers as shown in FIG. 4A (the oxygenator bundle 40 and the oxygenator exterior face 100 shown schematically in FIG. 4A for ease of illustration). In FIG. 4B, the depth filter 36 has at least a first filter layer 120 of level wound filaments optionally a second filter layer 122 of level wound filaments, and possibly additional filter layers (not shown) of level wound filaments on the second layer 122. The layers 120, 122 are annular, arranged about the central axis C described above, with various ones of the filaments 110 extending spirally around the central axis C. In some embodiments, the filaments 110 extend in differing directions along each of the layers 120, 122 such that each of the layers 120, 122 is composed of level cross-wound filaments. Alternatively, the filaments in one or both of the layers 120, 122 can be level wound without cross-winding. With the construction of FIGS. 4A and 4B, the layers 120, 122 can be characterized as cross-level wound or plan level composite wound filter layers 120, 122.

A minimum gap spacing 124 is established between axially or longitudinally adjacent ones of the filaments 110 within each of the first and second layers 120, 122. The phrases "axially adjacent" and "longitudinally adjacent" as used in this disclosure are in reference to two filaments (or fibers) immediately above or below one another and having aligned center points that intersect in a plane parallel to the central axis C. Thus, relative to the first filter layer 120, axially or longitudinally adjacent filaments 110a, 110b establish the minimum gap spacing identified at 124a; similarly, the filaments 110c, 110d of the second filter layer 122 establish the minimum gap spacing identified at 124b. It will be understood that with certain manufacturing techniques envisioned by the present disclosure, in some regions of the depth filter 36, a larger gap may exist between axially adjacent filaments 110. By minimizing a size of the minimum gap spacings 124 (e.g., on the order of 40 microns), radial blood flow through the filter layers 120, 122 provides enhanced filtration efficiency for a given size of microemboli. Although the depth filter 36 has been described as having two of the filter layers 120, 122, in other embodiments, three or four or more of the layers of level wound filaments can be formed by the filaments 110, with each successive layer being radially outward of the previous layer. Regardless, and as reflected in FIG. 4B, the first filter layer 120 is formed directly on the oxygenator exterior face 100 such that the filaments 110 of the first layer 120 physically contact the fibers 102 of the oxygenator exterior face 100.

Figure 5:
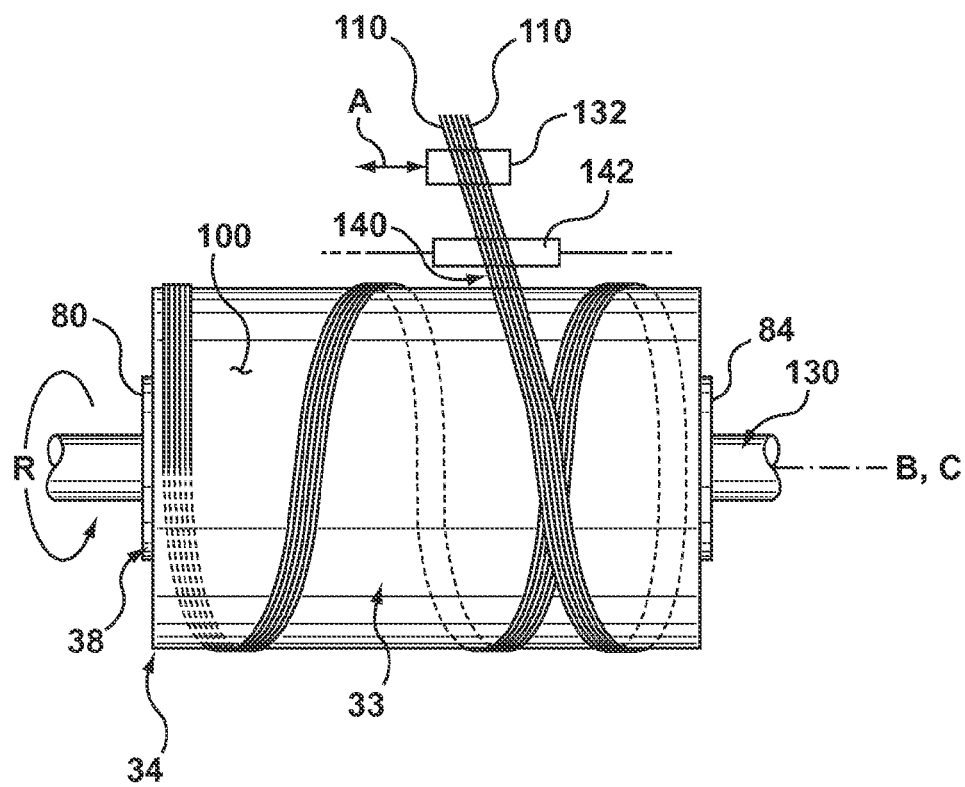
FIG. 5 is a simplified side view of a winding apparatus applying the depth filter of FIG. 3A to the oxygenator bundle of FIG. 3A in accordance with principles of the present disclosure.

In some embodiments, the filaments 110 are applied to the oxygenator exterior face 100 via a winding operation. The filament winding process may be conveniently performed on an apparatus of the type illustrated schematically in FIG. 5, that optionally may also be employed for winding the oxygenator bundle 40 onto the internal core 38. In general terms, the filament winding apparatus comprises a rotating mounting member 130 and a guide head 132. The rotating mounting member 130 rotatably maintains the internal core 38 (referenced generally), and thus the previously-formed oxygenator bundle 40 (the exterior face 100 of which is partially visible and drawn schematically in FIG. 5 for ease of explanation). The guide head 132 is arranged to travel reciprocally as illustrated by a double-headed arrow line A in FIG. 5 with respect to a longitudinal axis B of the mounting member 130 (i.e., the line of travel A of the guide 132 is parallel to the axis of rotation B of the mounting member 130).

As described, for example, in U.S. Pat. No. 4,975,247, the guide head 132 maintains a number of fiber guides (e.g., tubes, holes, pins, etc.) through which the filaments 110 are threaded as they enter the guide head 132 from a supply container (not shown). Upstanding ribs, grooves, guide pins, tubes, etc., may be used to space the filaments 110 at the guide head 132. Commercially available winding apparatus are available for wrapping the continuous filaments 110 on the oxygenator bundle 40. For example, Entec of Salt Lake City, Utah offers a winding apparatus with electronic gearing for varying the rotational speed of the mounting member 130 and the traverse speed of the guide head 132 during winding. The internal core 38 of the oxygenator 34 is mounted on the mounting member 130, with central axis C of the oxygenator 34 thus aligned with the axis of rotation B. The guide head 132 is then positioned at the left hand side (as viewed in FIG. 5) of the oxygenator bundle 40. A ribbon 140 of continuous filaments 110 (e.g., six of the filaments 110) is threaded through the fiber guides of the guide head 132. The leading end of the filament ribbon 140 is affixed to the oxygenator exterior face 100 extended at the far left end thereof. Rotation of the mounting member 130 is begun in the direction indicated by arrow R in FIG. 5. Motion of the guide head 132 is synchronized with rotation of the mounting member 130, and automatically travels axially of the oxygenator bundle 40 as the mounting member 130 rotates. It will be recognized by those skilled in the art that the guide head 132 travels axially a fixed distance for each revolution of the mounting member 130.

The guide head 132 travels from the first end 80 (left hand side of FIG. 5) of the internal core 38 to the second end 84 (right hand side of FIG. 5) where it decelerates. After decelerating, the guide head 132 reverses direction, accelerates and travels back to its starting position. After decelerating again and reversing direction, the guide head 132 begins its travel cycle anew. Alternatively, the guide head 132 may stop and dwell at the end points of the traverse. The reciprocal travel for the guide head 132 and the concurrent rotation of the mounting member 130 on which the oxygenator 34 has been mounted is continued until a depth filter filament bundle of desired diameter has been wound onto the oxygenator bundle 40, with the back-and-forth cycling of the guide head 132/ribbon 140 creating the level cross-wound layers described above.

As explained more fully at column 10, line 23 through column 11, line 62 of the '247 Patent, in the left-to-right travel of the guide head 132, the filament ribbon 140 is wound spirally around the oxygenated bundle 40, and the individual filaments 110 in the ribbon 140 are laid down in contact with the oxygenator exterior face 100. In the subsequent second traverse (right-to-left in FIG. 5) of the guide head 132, the filament ribbon 140 continues to be spirally wound onto the oxygenator bundle 40. Portions of the filaments 110 laid down during the second traverse of the guide head 132 contact previously-applied filaments 110 at certain crossover points. Except for these crossover points at which there is filament-to-filament contact with the filaments 110 laid down during the first traverse of the guide head 132, the filaments 110 laid down during the second traverse of the guide head 132 come into direct contact with the oxygenator exterior face 100. In the winding procedure being discussed, the oxygenator exterior face 100 is covered, except for the gap spacing 124 (FIG. 4B) between adjacent filaments 110. Filaments of the ribbon 140 laid down at a later traverse of the guide head 132 will be in radial registry with the filaments 110 laid down during an earlier traverse of the guide head 132 as described in the '247 Patent.

With embodiments in which the depth filter 36 (FIG. 3A) is formed by winding the filaments 110 onto the oxygenator bundle 40 as described above, the ratio of the mounting member 130 rotational speed relative to the traverse motion of the guide head 132 can be adjusted incrementally during the winding operation, thereby adjusting a wind angle of the filament ribbon 140. With this approach, a packing fraction of the filaments 110 along radial a thickness of the depth filter 36 is affected to provide a radially increasing packing fraction. Alternatively, or in addition, a tension of the filaments 110 can be regulated during the winding process. In particular, an optional roller 142 can be employed to apply tension to the ribbon 140. The roller 142 may rotate in response to the fiber ribbon 140 moving against it or may be driven so that its rotation matches the speed of the ribbon 140. Where the tension of the filaments 110 is increased during winding, an increasing packing fraction is obtained in a radially outward direction; thus, a force of the roller 142 against the filaments 110 can be increased to increase the resultant packing fraction. As a further alternative, a spacing between two (or more) filaments being simultaneously wound may be decreased during the winding operation, either incrementally or continuously, to increase packing fractions in a radially outward direction as described, for example, in the '619 Patent. In other embodiments, the packing fraction can be constant or decreasing in the radially outward direction. In yet other embodiments, the filaments 110 can be wound on a more individual basis (e.g., the continuous ribbon 140 technique described above need not be employed).

In some embodiments, the winding apparatus described above is employed to form the oxygenator bundle 40 about the internal core 38. For example, the internal core 38 is initially assembled to the rotating mounting member 130, and the guide head 132 employed to apply a ribbon of the fibers 102 (FIG. 3B) onto the internal core 38. Following formation of the oxygenator bundle 40, the fibers 102 are removed from the fiber guides (e.g., withdrawn from the tubes carried by the guide head 132), and replaced with the filaments 110 as described above. Thus, the depth filter 36 can optionally be formed over the oxygenator bundle 40 immediately after applying the fibers 102 to the internal core 38 and without removing the so-formed oxygenator 34 from the winding apparatus.

While the depth filter 36 has been described as being wound directly onto the oxygenator bundle 40, other constructions are also acceptable. For example, the depth filter 36 can be formed or provided apart from the oxygenator bundle 40 as a filament mat, comprising two or more plies. U.S. Pat. No. 4,940,617 describes two-ply (or multi-ply) mats having parallel fibers interconnected by cross-stitching where the fibers in one ply form an angle relative to the fibers in an adjacent ply or layer. The '617 Patent also shows the construction of bundles by winding such mats onto a core. Column 3, line 26 through column 14, line 67, including the figures referenced therein, contain the disclosure of such mats and bundles and the teachings of which are incorporated herein by reference, it being understood that the filaments 110 of the present disclosure could be used as the fibers of the '617 Patent. In general terms, and as shown in FIG. 6A, a filament mat 150 useful as the depth filter 36 (FIG. 2A) in accordance with the present disclosure consists of the filaments 110 combined into groups or plies 152, 154 by special disposition of inserted transverse fibers 156 or the like. In some constructions, and as shown in FIG. 6B for one of the plies 152, an interval between some of the filaments 110 can vary from the interval between others of the filaments 110. A gap 158, formed by this disposition of filament ends, between the filament groups, permits better penetration of the medium flowing around the filaments 110 in the resultant mat 150. Returning to FIG. 6A, the additional transverse fibers 154 or the like, and inserted in the middle of the filaments 110, are disposed such that they hold the filaments 110 at a regular, essentially identical interval to each other. Regardless of an exact construction, and with cross-reference to FIG. 3A, the mat 150 is rolled or wrapped about the exterior face 100 of the oxygenator bundle 40, and forms the depth filter 36 having at least the first and second level cross-wound filter layers as described above.

Figure 7:
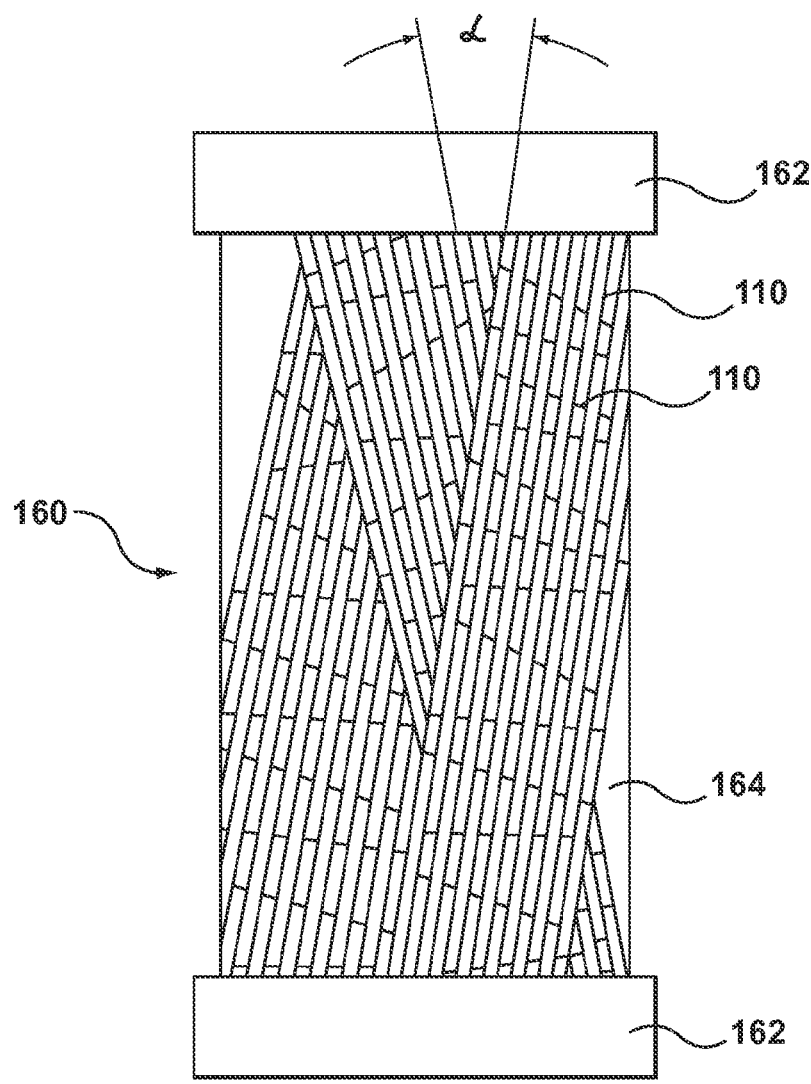
FIG. 7 is a simplified schematic illustration of a double weft tape useful as the depth filter of the devices of FIGS. 2A-2C.

In yet another acceptable embodiment, the depth filter 36 is provided as a woven filament double weft tape as described, for example, in U.S. Pat. No. 5,141,031, the entire teachings of which are incorporated herein by reference. In general terms, and as shown in FIG. 7, a double weft tape 160 including a plurality of the filaments 110 are embedded in head plates 162. Typically, the filament ends are embedded by spinning them into a curable potting compound. Regardless, the double weft tape 160 provides various filament tapes arranged in layers around a core 164 (e.g., the oxygenator bundle 40 (FIG. 3A)) in such a way that the filaments 110 of adjacent layers form layers with an angle α that is not greater than 30° in some embodiments. The double weft tape 160 is akin to the two-ply mat 150 (FIG. 6A) described above, but typically exhibits a more narrow width. The tape 160 can be wrapped or wound about the oxygenator exterior face 100 (FIG. 3A) to form the depth filter 36 as described above.

Returning to FIGS. 4A and 4B, regardless of an exact construction of the depth filter 36 and corresponding assembly to the oxygenator bundle 40, the first and second filter layers 120, 122 of level wound filaments establish a tortuous radial flow path for blood flow through the depth filter 36. Thus, the depth filter 36 is markedly different from the screen or mesh construction associated with conventional arterial filters. In other words, the radial flow paths (i.e., gap spacings) between the filaments 110 of the first layer 120 are not radially aligned with those of the second layer 122, thus defining a "depth" to the depth filter 36. In contrast, with screen or mesh filters, the flow path spacing are radially open or "linear" through a thickness of the material. The minimum gap spacings 124 between the filaments 110 and the number of filter layers are two of the factors that determine the efficiency of the depth filter 36 for a given size of microemboli. Further, the gap spacings 124 between the filaments 110, the outer diameter of the filaments 110, and the crossing angle of the filaments 110 determine a percentage of open area of the depth filter 36. By employing reduced outer diameter filaments (as compared to an outer diameter of the fibers 102 of the oxygenator bundle 40), the minimum gap spacings 124 between the filaments 110 can be reduced (as compared to the minimum gap spacings 104 (FIG. 3C) between the fibers 102 of the oxygenator bundle 40) without increasing the shear to which the blood flow is exposed. In some embodiments, the depth filter 36 is configured to filter or remove microemboli as understood in the art, for example particulate microemboli as small as 15 micron, and gaseous microemboli (i.e., bubbles) on the order of 250 microns or less. With embodiments in which the filaments 110 are microporous gas conducting hollow filaments, a pressure drop across the depth filter 36 will provide a favorable pressure gradient to drive gaseous microemboli through the pores and into the lumens of the filaments 110. The gas from the so-captured gaseous microemboli can be vented to the atmosphere through the gas outlet 68 (FIG. 2A) associated with the oxygenator bundle 40, or to a separate manifold.

Figure 8:
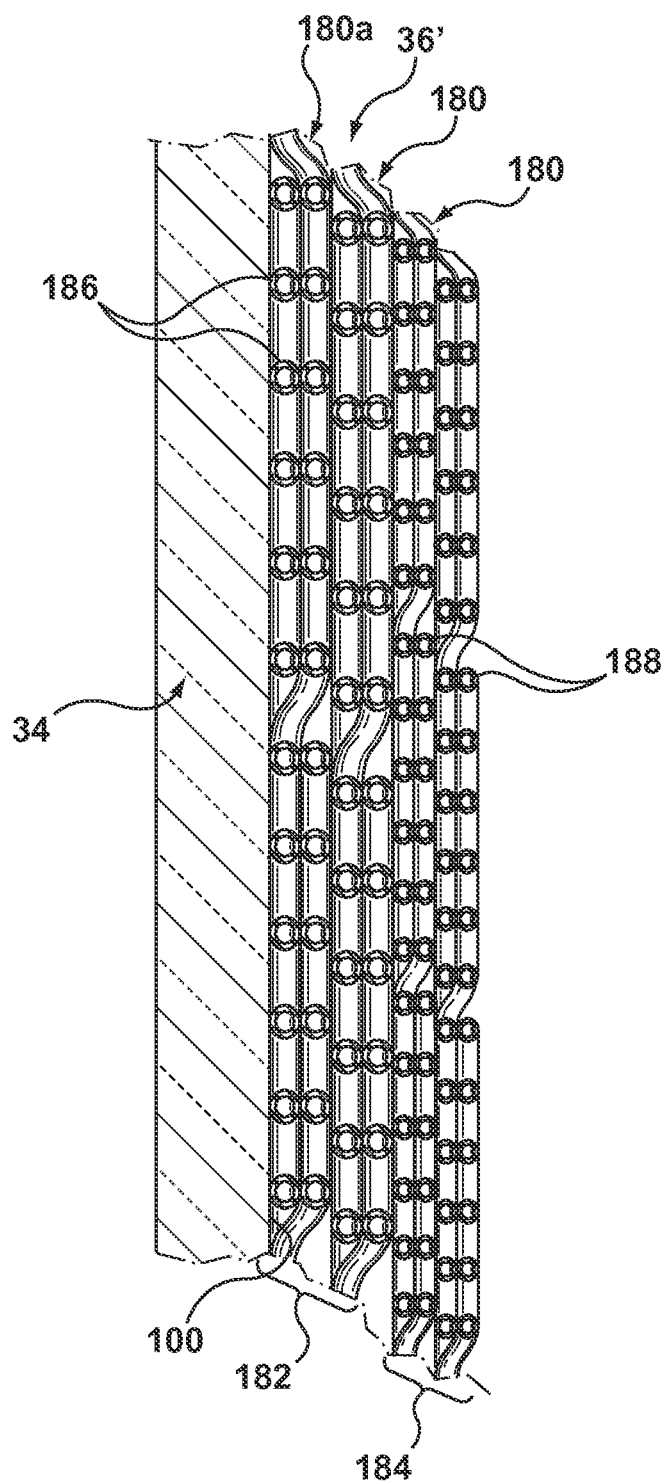
FIG. 8 is a cross-sectional, greatly magnified view of an alternative depth filter useful with the devices of FIGS. 2A-2C.

While the depth filter 36 has been described as utilizing relatively uniform filaments across a radial thickness of the depth filter 36, in other constructions, variations in the filaments 110 can be incorporated. For example, FIG. 8, illustrates, in simplified form, a portion of an alternative depth filter 36' in accordance with the present disclosure. The depth filter 36' is akin to previous embodiments, and includes a plurality of level wound filaments combining to define two or more filter layers 180. As a point of reference, the inner most layer 180a is placed in direct physical contact with the exterior face 100 of the oxygenator bundle 40 (illustrated schematically) upon final assembly. Various differences are incorporated into one or more of the layers 180 to create two (or more) filtering zones 182, 184 exhibiting different filtration characteristics or properties. For example, filaments 186 of the first zone 182 can be hollow, whereas filaments 188 of the second zone 184 are solid (or vice-versa); as a result, the first zone 182 more readily filters or removes gaseous microemboli, whereas the second zone 184 more actively filters particulate microemboli. Other differences, such as filament materials, minimum gap spacings, packing fraction, etc., can alternatively or additionally be incorporated in the zones 182, 184 to provide desired dual functioning filtration.

Returning to FIG. 3A, although in certain respects the level cross-woven layers of the depth filter 36 are akin to the oxygenator bundle 40, one or more structural differences exist between the depth filter 36 and the oxygenator bundle 40. In general terms, these differences are uniquely selected to promote functioning of the oxygenator bundle 40 to oxygenate (and remove carbon dioxide from) blood flow, whereas the depth filter 36 removes or filters gaseous and particulate microemboli. For example, in some embodiments, the plastic resin of the depth filter filaments 110 differs from the plastic resin of the oxygenator bundle fibers 102 (e.g., the depth filter filaments 110 are formed of polyester, poly methyl pentene, or silicone, whereas the oxygenator bundle fibers 102 are formed of polypropylene). In other embodiments, the oxygenator bundle fibers 102 are hollow, whereas at least some of the depth filter filaments 110 are solid. In yet other embodiments, an outer diameter of the oxygenator bundle fibers 102 is greater than an outer diameter of the depth filter filaments 110 (e.g., the oxygenator bundle fibers 102 have an average outer diameter in the range of 200-300 microns, whereas the depth filter filaments 110 have an average outer diameter in the range of 100-250 microns). In yet other embodiments, the minimum gap spacing between axially adjacent ones of the oxygenator bundle fibers 102 is less than the minimum gap spacing between axially adjacent ones of the depth filter filaments 110 (e.g., the minimum gap spacing between axially adjacent ones of the oxygenator bundle fibers 102 is in the range of 75-150 microns, whereas the minimum gap spacing between axially adjacent ones of the depth filter filaments 110 is in the range of 40-75 microns). In yet other embodiments, a packing fraction of the depth filter 36 is higher than the packing fraction at the exterior face 100 of the oxygenator bundle 40. Alternatively, or in addition, a wind angle associated with the fibers 102 of the oxygenator bundle 40 differs from the wind angle associated with the filaments 110 of the depth filter 36. In some constructions, two or more of the above-described differences are incorporated into the depth filter 36 and the oxygenator bundle 40.

Figure 9:
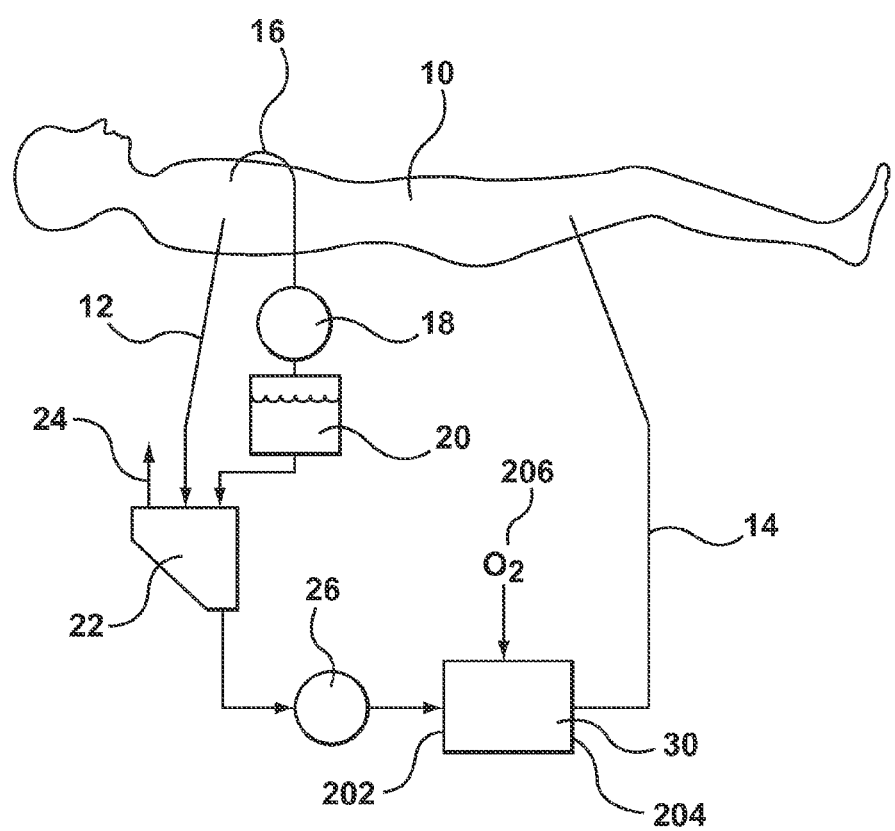
FIG. 9 is a schematic diagram of an extracorporeal blood circuit incorporating the devices of FIGS. 2A-2C in accordance with principles of the present disclosure.

The combination oxygenator and arterial filter device 30 can be incorporated into an extracorporeal blood circuit 200 as shown in FIG. 9. In general terms, the extracorporeal blood circuit 200 can be akin to any extracorporeal blood circuit commonly employed, and generally includes the venous return line 12, the cardiotomy pump and reservoir 20, the venous blood reservoir 22, and the arterial line 14 as described above. The combination oxygenator and arterial filter device 30 is fluidly connected to the venous line 12, for example via an inlet side 202. An outlet side 204 of the device 30 is fluidly connected to the arterial line 14. A source of oxygenating gas 206 is fluidly connected to the device 30, establishing an oxygenating gas flow path to the hollow fibers 102 (FIG. 3C) of the oxygenator bundle 40 (FIG. 3A). In some embodiments, the oxygenating gas flow path is fluidly closed relative to the depth filter filaments 110 (FIG. 3A). Additional components can be interposed within the circuit 200. However, in accordance with embodiments of the present disclosure, the device 30 provides necessary arterial filtration, such that a separate or additional arterial filter is not included between the device 30 and the arterial line 14. As compared to conventional extracorporeal blood circuit configurations, then, an overall prime volume is reduced with use of the device 30. The extracorporeal blood circuit 200 is thus simplified as one less component need be fluidly connected into the circuit 200.

EXAMPLES

The following examples and comparative examples further describe the combination oxygenator and arterial filter devices of the present disclosure. The examples are provided for exemplary purposes to facilitate an understanding of the present disclosure, and should not be construed to limit the disclosure to the examples.

Example combination oxygenator and arterial filter devices (Examples 1-6) were constructed by forming a depth filter directly over the oxygenator bundle of a commercially available oxygenator (an Affinity® NT Oxygenator available from Medtronic, Inc., of Minneapolis, Minn., the fibers of which were coated with a Trillium® Biosurface available from BioInteractions, Ltd., UK). The integrated arterial depth filter was formed by spiral or cross-winding filaments in predetermined fashions to establish two or more filter layers of level cross-wound filaments, including a designated gap spacing between axially adjacent filaments. The filament outer diameter, number of filter layers, and gap spacing for each of Examples 1-6 are set forth in the Table below.

The filtration efficiency of the combination oxygenator and arterial filter devices of Examples 1-6 was tested by flowing a particle-laden fluid through the device, and determining the percentage of particles captured or retained by the device. The particles were latex microspheres, and batches of differently-sized particles were employed with separate tests for each sample. For each test, the difference between the number or weight of the particles introduced to the device and number or weight of particles captured by the device were recorded and used to determine filtration efficiency. The particle size for each test is shown in the Table below, along with the determined filtration efficiency.

To evaluate the filtration efficiency performance of the example combination oxygenator and arterial filter devices, commercially available arterial filters and commercially available oxygenators were subjected to the tests descried above, and the results recorded. In particular, Comparative Examples 1 and 2 were commercially available arterial filters (Affinity® Arterial Filter (38 micron filament gap)) coated with Trillium® Biosurface. Comparative Examples 3 and 4 were commercially available arterial filters (Affinity® Arterial Filter) coated with Carmeda® Biosurface (available from Carmeda AB of Sweden). Comparative Examples 5 and 6 were commercially available oxygenators (Affinity® NT Oxygenator available from Medtronic, Inc., of Minneapolis, Minn.) coated with Carmeda® Biosurface. Comparative Examples 7 and 8 were commercially available oxygenators (Affinity® NT Oxygenator) coated with Trillium® Biosurface. The test results are provided in the Table below.

standalone oxygenator and arterial filter products. The combination devices of Examples E1-E6 effectively replace the separate arterial filters (CE1-CE4) and oxygenators (CE5-CE8), and thus reduce an overall prime volume. As shown, the combination sample devices exhibited equal or better filtration efficiency as compared to the individual arterial filters or oxygenators.

Although the present disclosure has been described with reference to preferred embodiments, workers skilled in the art will recognize that changes can be made in form and detail without departing from the spirit and scope of the present disclosure.

What is claimed is:

1. A combination oxygenator and arterial filter device for treating blood in an extracorporeal blood circuit, the device comprising:
    a housing;
    an oxygenator maintained within the housing and including a plurality of hollow microporous fibers helically wound about an internal core to define an oxygenator bundle forming an oxygenator exterior face; and
    a depth filter disposed directly over the oxygenator exterior face, the depth filter including a plurality of filaments arranged to define a first filter layer of level wound filaments directly abutting the oxygenator exterior face and a second filter layer of level wound filaments directly abutting the first filter layer opposite the oxygenator exterior face;
    wherein a structure of the oxygenator bundle differs from a structure of the depth filter by at least one characteristic selected from the group consisting of: materials of the fibers and filaments, construction of the fibers and the filaments, and minimum gap spacings between axially adjacent ones of the fibers and axially adjacent ones of the filaments.

2. The device of claim 1, wherein an outer diameter of the filaments is less than an outer diameter of the fibers.

3. The device of claim 2, wherein an outer diameter of the filaments is not greater than 300 microns.

4. The device of claim 1, wherein the filaments are hollow filaments, and wherein an inner diameter of the filaments is less than an inner diameter of the fibers.

TABLE

| | Filtration Efficiency | | | | Integrated Arterial Filter | | |
| --- | --- | --- | --- | --- | --- | --- | --- |
| | | | | | Filament | | # |
| Sample | 20 μm particles | 45 μm particles | 65 μm particles | 90 μm particles | OD (microns) | Gap (microns) | Crossing Layers |
| E1 | 34.9% | 94.6% | 99.1% | 100.0% | 200 | 58 | 2 |
| E2 | 56.2% | 98.8% | 100.0% | 100.0% | 130 | 58 | 6 |
| E3 | 57.9% | 97.2% | 99.9% | 99.9% | 130 | 58 | 6 |
| E4 | 41.4% | 94.8% | 99.4% | 100.0% | 200 | 58 | 2 |
| E5 | 19.2% | 95.4% | 99.7% | 99.9% | 130 | 58 | 2 |
| E6 | 38.1% | 92.8% | 99.1% | 100.0% | 130 | 51/51 | 2 |
| CE1 | 11.7% | 100.0% | N/A | N/A | NA | 38 | NA |
| CE2 | 35.0% | 99.8% | N/A | N/A | NA | 38 | NA |
| CE3 | 37.8% | 99.8% | N/A | N/A | NA | 38 | NA |
| CE4 | 12.7% | 100.0% | N/A | N/A | NA | 38 | NA |
| CE5 | 54.5% | 95.9% | 99.7% | 100.0% | NA | NA | NA |
| CE6 | 45.4% | 94.6% | 99.1% | 99.2% | NA | NA | NA |
| CE7 | 41.2% | 92.6% | 99.1% | 100.0% | NA | NA | NA |
| CE8 | 17.6% | 90.8% | 98.9% | 100.0% | NA | NA | NA |

The test results reveal that the combination oxygenator and arterial filter devices of the present disclosure were highly beneficial in filtration efficiency as compared to separate, 5. The device of claim 1, wherein an entirety of the filaments are solid filaments.

6. The device of claim 1, wherein the filaments include hollow filaments and solid filaments.

7. The device of claim 1, wherein the fibers are formed of a first material and the filaments are formed of a second material differing from the first material.

8. The device of claim 1, wherein a minimum gap spacing between axially adjacent filaments of the first filter layer is less than a minimum gap spacing between axially adjacent fibers of the oxygenator bundle.

9. The device of claim 8, wherein the minimum gap spacing between axially adjacent filaments of the first filter layer is not less than 40 microns.

10. The device of claim 1, wherein a packing fraction of the depth filter is greater than a packing fraction of the oxygenator exterior face.

11. The device of claim 1, wherein the filaments are wound over the oxygenator bundle.

12. The device of claim 1, wherein the filaments are knitted into a mat, and further wherein the mat is rolled over the oxygenator exterior face.

13. The device of claim 1, wherein the filaments are knitted into a double weft tape, and further wherein the double weft tape is applied over the oxygenator exterior face.

14. The device of claim 1, wherein the housing includes an inlet and an outlet, and defines a blood flow path from the inlet, radially through the oxygenator bundle, radially through the depth filter, and to the outlet.

15. The device of claim 14, wherein the depth filter establishes a radially tortuous blood flow path.

16. The device of claim 1, wherein the filaments of the depth filter further define:
 a third filter layer of level wound filaments directly abutting the second filter layer opposite the first filter layer; and
 a fourth filter layer of level wound filaments directly abutting the third filter layer opposite the second filter layer.

17. The device of claim 1, wherein the oxygenator bundle is configured to remove carbon dioxide from venous blood flowing through the oxygenator bundle, and the depth filter is configured to remove particulate and gaseous microemboli from blood flowing through the depth filter.

18. The device of claim 1, wherein the first and second filter layers are each composed of level cross-wound filaments.

19. An extracorporeal blood circuit comprising:
 a venous line for receiving venous blood from a patient;
 an arterial line for delivering blood to a patient; and
 a combination oxygenator and arterial filter device having an inlet side fluidly connected to the venous line and an outlet side fluidly connected to the arterial line, the device comprising:
 a housing,
 an oxygenator maintained within the housing and including a plurality of hollow microporous fibers helically wound about an internal core to define an oxygenator bundle forming an oxygenator exterior face,
 a depth filter disposed directly over the oxygenator exterior face, the depth filter including a plurality of filaments arranged to define a first filter layer of level wound filaments directly abutting the oxygenator exterior face and a second filter layer of level wound filaments directly abutting the first filter layer opposite the oxygenator exterior face,
 wherein a structure of the oxygenator bundle differs from a structure of the depth filter by at least one characteristic selected from the group consisting of: materials of the fibers and filaments, construction of the fibers and the filaments, and minimum gap spacings between axially adjacent ones of the fibers and axially adjacent ones of the filaments.

20. The extracorporeal blood circuit of claim 19, wherein the circuit is characterized by the absence of an additional arterial filter between the device and the arterial line.

21. The extracorporeal blood circuit of claim 19, further comprising:
 a source of gas fluidly coupled to the hollow fibers and fluidly closed to the filaments.

22. A method of making a combination oxygenator and arterial filter device for treating blood in an extracorporeal blood circuit, the method comprising:
 helically winding a plurality of hollow microporous fibers about an internal core to define an oxygenator bundle forming at an oxygenator exterior face;
 applying a depth filter directly over the oxygenator exterior face, the depth filter including a plurality of filaments arranged to define a first filter layer of level wound filaments directly abutting the oxygenator exterior face and a second filter layer of level wound filaments directly abutting the first filter layer opposite the oxygenator exterior face;
 wherein a structure of the oxygenator bundle differs from a structure of the depth filter by at least one characteristic selected from the group consisting of: materials of the fibers and filaments, construction of the fibers and the filaments, and minimum gap spacings between axially adjacent ones of the fibers and axially adjacent ones of the filaments; and
 disposing the oxygenator bundle and the depth filter within a housing.

23. The method of claim 22, wherein applying a depth filter includes helically winding the plurality of filaments over the oxygenator bundle to establish the first and second filter layers as each being composed of level cross-wound filaments.

24. The method of claim 23, wherein helically winding the plurality of hollow microporous fibers includes threading a fiber guide of a winding apparatus with the hollow fibers and rotating the internal core relative to the fiber guide, and further wherein helically winding the plurality of filaments includes:
 removing the hollow fibers from the fiber guide;
 threading at least some of the filaments into the fiber guide; and
 rotating the internal core relative to the fiber guide.

25. The method of claim 22, wherein an outer diameter of the filaments is less than an outer diameter of the fibers.

26. The method of claim 22, wherein the filaments are solid.

27. The method of claim 22, wherein the fibers are formed of a first material and the filaments are formed of a second material differing from the first material.

28. The method of claim 22, wherein a minimum gap spacing between axially adjacent filaments of the first filter layer is less than a minimum gap spacing between axially adjacent fibers of the oxygenator bundle.

* * * * *